(12) United States Patent
Chakravorty et al.

(10) Patent No.: US 7,056,530 B1
(45) Date of Patent: Jun. 6, 2006

(54) SELFEMULSIFIABLE FORMULATION HAVING ENHANCED BIOABSORPTION AND IMMUNOSUPPRESSION ACTIVITIES

(75) Inventors: Saibal Chakravorty, Mumbai (IN); Prasad Bharti, Maharashtra Pin (IN)

(73) Assignee: RPG Life Sciences Ltd., Mumbai (IN)

( * ) Notice: Subject to any disclaimer, the term of this patent is extended or adjusted under 35 U.S.C. 154(b) by 361 days.

(21) Appl. No.: 10/380,598

(22) PCT Filed: Sep. 18, 2000

(86) PCT No.: PCT/IN00/00091
§ 371 (c)(1),
(2), (4) Date: Mar. 17, 2003

(87) PCT Pub. No.: WO02/22158
PCT Pub. Date: Mar. 21, 2002

(51) Int. Cl.
*A61K 9/48* (2006.01)
*A61K 9/66* (2006.01)

(52) U.S. Cl. .................... 424/455; 424/451
(58) Field of Classification Search ............ 424/400, 424/455, 456, 451, 452; 514/937
See application file for complete search history.

(56) References Cited

U.S. PATENT DOCUMENTS

| | | | |
|---|---|---|---|
| 2,870,062 A | 1/1959 | Stanley et al. | |
| 4,388,307 A | 6/1983 | Cavanak | |
| 5,589,455 A | 12/1996 | Woo | |
| 5,858,401 A | 1/1999 | Bhalani et al. | |
| 5,985,321 A | 11/1999 | Brox et al. | |
| 6,024,978 A | 2/2000 | Hauer et al. | |
| 6,267,985 B1 * | 7/2001 | Chen et al. | 424/451 |
| 6,284,268 B1 * | 9/2001 | Mishra et al. | 424/455 |

FOREIGN PATENT DOCUMENTS

| | | |
|---|---|---|
| EP | 0 982 035 A1 | 1/2000 |
| WO | WO 97/48410 | 12/1997 |

* cited by examiner

*Primary Examiner*—Thurman Page
*Assistant Examiner*—S. Tran
(74) *Attorney, Agent, or Firm*—James Ray & Assoc.

(57) ABSTRACT

A selfemulsifiable formulation comprising a lipophilic system consisting of a medium chain triglyceride of caprylic acid and capric acid, and of labrasol, wherein labrasol also serves as a surfactant, which is combined with other selected surfactants, like cremophore RH 40 and/or polysorbate 80 and wherein the formulation also comprises immunosuppression agent, essentially cyclosporine, hydrophilic agent preferably ethanol, antioxidant preferably alpha-tocopherol and preservative preferably benzyl alcohol. The formulation is prepared by dissolving immunosuppression agent in hydrophilic agent followed by entrapping with lipophilic agent and subsequent treatment with surfactants, preservative and anioxidant. The formulation is filled in a soft-gelatin shell capable of rupturing in less than 10 minutes to deliver the formulation in an upper part of the gastrointestinal tract, wherein it forms thermodynamically stable oil in water microemulsions in situ to have enhanced bioavailability and bioabsorption of immunosuppression agent, which can show its enhanced immunosuppression activites thereby.

18 Claims, 6 Drawing Sheets

FIGURE 6

| Exp. No. → Amount in % Composition mg by weight → Ingredient ↓ | I | II | III | IV | V | VI | VII | VIII | IX | X | XI | XII | XIII | XIV | XV |
|---|---|---|---|---|---|---|---|---|---|---|---|---|---|---|---|
| Cyclosporine | 10.00 | 10.00 | 10.00 | 10.00 | 10.00 | 10.00 | 10.00 | 10.00 | 10.00 | 10.00 | 10.00 | 10.00 | 10.00 | 10.00 | 10.00 |
| Ethanol (Dehydrated) | 11.88 | 9.50 | 9.50 | 9.50 | 9.50 | 9.50 | 9.50 | 10.45 | 10.45 | 10.45 | 10.45 | 10.45 | 10.45 | 9.50 | 12.40 |
| Labrafac Lipophile | --- | --- | 12.00 | 12.00 | --- | --- | --- | --- | 5.00 | --- | --- | 1.00 | --- | 15.20 | 17.84 |
| Labrasol | 25.21 | 23.40 | 38.49 | 46.51 | 46.51 | 58.50 | 40.50 | 84.05 | 59.55 | 39.77 | 82.55 | 82.05 | 82.55 | 33.60 | 59.76 |
| Cremophore RH 40 | --- | --- | --- | --- | --- | --- | --- | --- | --- | 39.77 | --- | --- | --- | 28.00 | 25.00 |
| Polysorbate 80 | 25.61 | 21.60 | 30.00 | 30.01 | 30.00 | 30.00 | --- | --- | --- | --- | 0.50 | 0.50 | 0.50 | 12.38 | 13.76 |
| Crodonol GTC/C | 40.00 | --- | --- | --- | 12.00 | --- | --- | --- | --- | --- | --- | --- | 0.50 | --- | --- |
| Capmul MCM | --- | 35.50 | --- | --- | --- | --- | 20.00 | 0.50 | --- | 5.00 | 0.50 | --- | --- | --- | --- |
| Propylene glycol | --- | --- | --- | --- | --- | --- | 20.00 | 5.00 | 5.00 | 5.00 | 5.00 | 5.00 | 5.00 | --- | --- |
| Benzyl alcohol | --- | --- | --- | --- | --- | --- | --- | 1.00 | 1.00 | 1.00 | 1.00 | 1.00 | 1.00 | 0.68 | 1.00 |
| Alpha-tocopherol | 0.0009 | .0009 | .0009 | .0009 | .0009 | .0009 | 0.0009 | 0.0009 | 0.0009 | 0.0009 | 0.0009 | 0.0009 | 0.0009 | 0.00008 | 0.0001 |

SELFEMULSIFIABLE FORMULATION HAVING ENHANCED BIOABSORPTION AND IMMUNOSUPPRESSION ACTIVITIES

TECHNICAL FIELD OF INVENTION

The present invention relates to a formulation, particularly to a selfemulsifiable formulation for oral administration having enhanced bioabsorption and immunosuppression activities, more particularly it relates to a selfemulsifiable formulation for early delivery of drug, even more particularly it relates to a selfemulsifiable formulation, which will form thermodynamically stable oil in water emulsion preferably in upper part of gastrointestinal tract and facilitate the early delivery of drug, particularly of the immunosuppression agent, still more particularly it relates to a selfemulsifiable formulation not only having the improved bioavailability and bioabsorption but also has improved capability to release the drug in reduced time with reduced toxicity and variability that is inter and intra patient bioabsorption variability. The present invention is particularly relates to a selfemulsifiable formulation, which facilitates increased solubility, transport rate, bioavailability and bioabsorption of an agent having immunosuppression activity.

BACKGROUND ART OF INVENTION

The immunosuppression activity of a drug acting as an immunosuppression agent is achieved by inhibiting the growth and differentiation of T-cells. Such immunosuppression agents also have other pharmacological activities like anti-inflammatory and/or antiparasitic, in particular antiprotozoal, like antimalerial activities. The commonly used immunosuppression agents include cyclosporine. There are many cyclosporines known in the art, like cyclosporine A, cyclosporine B, cyclosporine C, cyclosporine D, cyclosporine E etc. The cyclosporine A is preferably used in the clinical field due to its proven pharmacological activity and clinical indication and effectiveness.

This immunosuppression agent, that is, cyclosporine A has been found useful in various other areas, like in auto immune diseases, inflammatory conditions, particularly in inflammatory conditions with an aetiology including an autoimmune component like arthritis.

Further, this immunosuppression agent is applicable in rheumatoid arthritis, arthritis chronica, and progredientic and arthritis deformana. Further, this immunosuppression agent is also applicable in rheumatic diseases.

The immunosuppression therapy using this immunosuppression agent has been proposed or applied in autoimmune hematological disorder, like hemolytic anemia, aplastic anaemia, pure red cell anaemia and idiopathic thrombocytopaenia, systemic lupus erythematosus, dematomyositis, chronic active hepatitis, myasthenia gravis, psoriasis, Steven-Johnson syndrome, idiopathic spure, autoimmune inflammatory bowel disease including ulcerative colitis and crohn's disease, endocrine opthalmopathy, Graves disease, sarcoidosis, multiple sclerosis, primary billiary cirrhosis, juvenile diabetes, like diabetes mellitus Type I, anterior and posterior uveitis, and keratoconjuncativities sicca an vernal keratoconjuncativities, intestinal lung fibrosis, psoriatic arthritis and glomerulonephritis—with or without nephrotic syndrome, like idiopathic nephrotic syndrome or minimal change nephropathy.

Therefore, this immunosuppression agent is widely acceptable immunosuppression agent. This agent is made available in the form of pharmaceutical formulation. The clinical acceptance of such formulations comprising of this immunosuppression agent has suffered due to low solubility and low transport rate and delayed bioavailability and bioabsorption of the immunosuppression agent.

Therefore, in recent past the research has been directed to improve its solubility and transport rate. In addition efforts have been on to improve its early bioavailability, particularly in the upper part of the gastrointestinal tract and bioabsorption.

Various formulations, comprising this immunosuppression agent as one of the essential ingredients, have been developed and made available. Although there are many formulations to form microemulsions, but many of them do not have satisfactorily acceptable bioavailability and bioabsorption. The formation of microemulsions of the clinically acceptable particle size that is of less than 200 mm, particularly of less than 100 nm, is one of the desired requirements for the formulation to be clinically acceptable. Therefore, the efforts are still on to develop new formulations, particularly the formulations which will have better bioavailability, particularly in the upper part of the gastrointestinal tract and better bioabsorption and at the same time will have better solubility and reduced variability, that is inter and intra patient bioabsorption variability, and form the microemulsions of the clinically acceptable particle size.

The another parameter controlling the applicability of formulations of the immunosuppression agent is its manner of administration. The formulation comprising of the immunosuppression agent, particularly of this immunosuppression agent is generally administered after filling it in a soft or hard shell, known as capsule, or in the form of solution for oral administration. The solution form of formulation of the immunosuppression agent is taken after dilution with flavored milk or fruit juice. The mixing with milk or the juice forms the emulsion, particularly microemulsions of varying particle sizes, generally varying above 100 nm, preferably varying above 150 nm. The preferred form of administration of the formulation of this immunosuppression agent is after filling the formulation in a shell, which may be soft or hard shell.

The major problem arises, when the immunosuppression agent or its formulation is administered after filling in a hard or soft-shell. It has been generally observed that, the availability of the immunosuppression agent will depend upon the rupture time of the shell.

The known formulations of the immunosuppression agent, which are made available in the shell, have rupture time of shell varying from 12 minutes to 15 minutes or above. The problem arises due to this longer rupture time, which delays the availability of the immunosuppression agent, which in-turn effects its bioabsorption. The desired rupture time of the shell in order to make the availability of the immunosuppression agent at an early time, preferably in the upper part of the gastrointestinal tract is less than 12 minutes, preferably less than 10 minutes.

Need of Invention

Therefore, there is a need to have a formulation, particularly a selfemulsifiable formulation for oral administration, which can overcome all or some of the disadvantages and limitations of the prior art, as described herein above and more particularly of a selfemulsifiable formulation, which facilitates increased solubility, transport rate, bioavailability and bioabsorption of the immunosuppression agent.

OBJECTS OF INVENTION

This is the main object of the present invention to make a complete disclosure of a formulation, particularly of a selfemulsifiable formulation for oral administration, which can overcome all or some of the disadvantages and limitations of the prior art, as described herein above and more particularly of a selfemulsifiable formulation, which can facilitate the increased solubility, transport rate, bioavailability and bioabsorption of the immunosuppression agent.

Another object of this invention is to propose for a selfemulsifiable formulation capable of making early bioavailability of the immunosuppression agent, particularly in the upper part of the gastrointestinal tract.

Still another object of this invention is to propose a selfemulsifiable formulation, which can satisfactorily meet the clinical requirements.

Still further an object of the present invention is to disclose a selfemulsifiable formulation, which can form microemulsions of particle size less than 200 nm, preferably less than 100 nm.

Yet another object of this invention is to propose a selfemulsifiable formulation, which can administered orally after filling in a soft or hard shell, or in the form of solution.

This is further an object of this invention to disclose a selfemulsifiable formulation, which can form microemulsions of particle size less than 200 nm, preferably less than 100 nm and a clear solution when administered orally in the form of microemulsions, mixed with fruit juice, milk or any aqueous medium.

This is still an object of this invention to disclose a selfemulsifiable formulation, which can form microemulsions of particle size less than 200 nm, preferably less than 100 nm when administered orally after filling in a soft or hard shell.

This is yet an object of this invention to disclose a selfemulsifiable formulation, which on administration in a shell, particularly in a soft shell is made available at an early time, preferably in the upper part of the gastrointestinal tract in less than 12 minutes, more preferably in less than 10 minutes, by rupturing the shell in desired time of less than 12 minutes.

This is still an object of this invention to disclose a selfemulsifiable formulation, which has better solubility and reduced variability, that is inter and intra patient bioabsorption variability.

Still another an object of this invention is to disclose a selfemulsifiable formulation, which can be stored in the tropical countries for a longer time and can forms thermodynamically stable oil in water microemulsions in-situ, which are stable for more than 24 hrs.

Yet another an object of this invention is to disclose a selfemulsifiable formulation and the method of preparation thereof.

Further objects, advantages and preferred embodiments of the present invention will be more apparent from the following description when read in conjunction with the accompanying drawings, which are not intended to limit the scope of the present invention.

DESCRIPTION OF THE FIGURES

FIG. 6 shows the compositions of formulations prepared in accordance to the preferred method of the present invention.

BRIEF DESCRIPTION OF INVENTION

Figure 1:
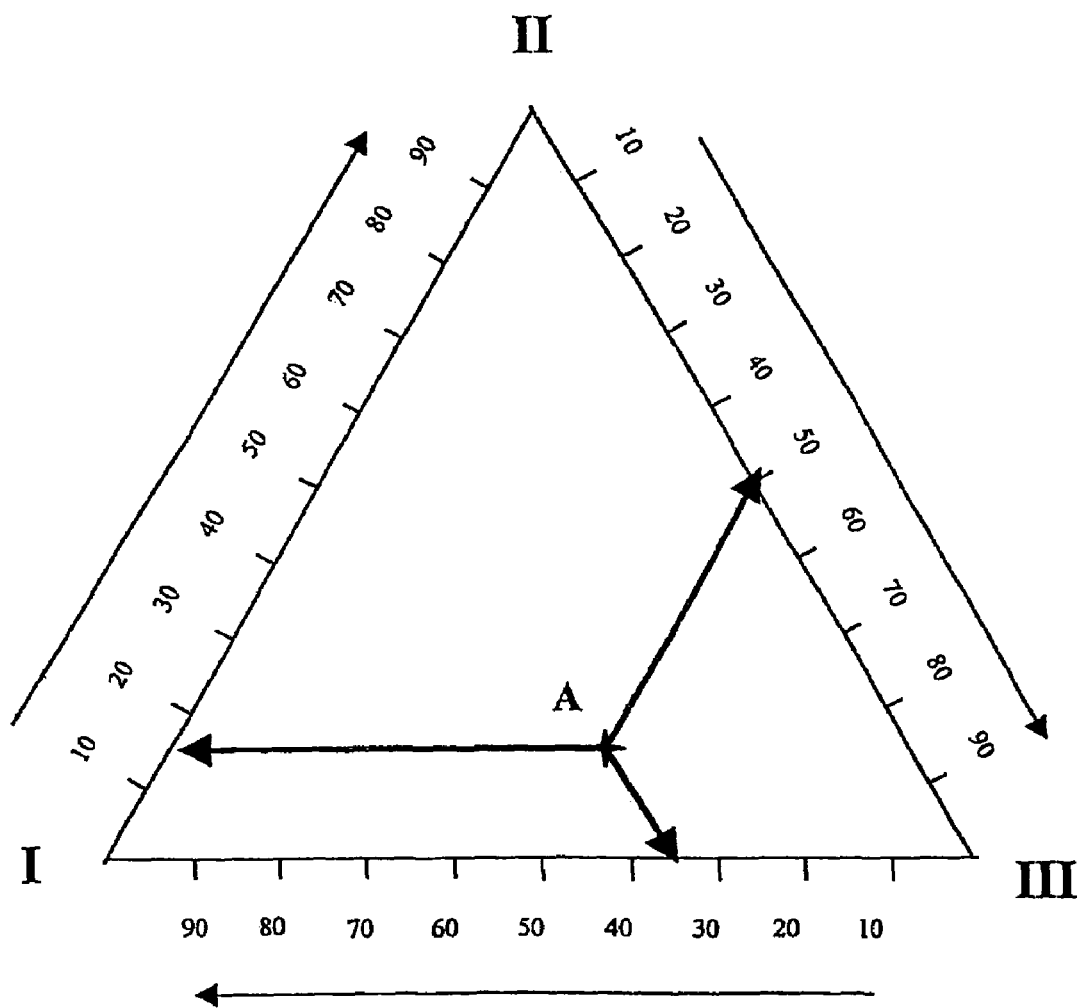
FIG. 1 shows the phase diagram of the selfemulsifiable formulation in accordance to the preferred embodiments of the present invention.

Accordingly this invention provides a complete disclosure of a formulation, particularly of a selfemulsifiable formulation for oral administration, which has enhanced bioabsorption and immunosuppression activities, more particularly of a selfemulsifiable formulation for early delivery of drug, even more particularly of a selfemulsifiable formulation, which will form thermodynamically stable bil in water emulsion preferably in upper part of gastrointestinal tract and facilitate the early delivery of drug, particularly of the immunosuppression agent, still more particularly of a selfemulsifiable formulation not only having the improved bioavailability and bioabsorption but also the improved capability to release the drug in reduced time with reduced toxicity and variability, that is inter and intra patient bioabsorption variability.

In accordance to the present invention a selfemulsifiable formulation is disclosed, which facilitates the increased solubility, transport rate, bioavailability and bioabsorption of an agent, particularly of an immunosuppression agent, wherein said formulation essentially comprises of immunosuppression agent, hydrophilic agent, lipophilic agent, one or more of surfactants, antioxidant and preservative. In accordance to one of the preferred embodiments of the present invention the formulation is made available in a shell; preferably soft shell, wherein the said shell essentially comprises of gelatin, glycerin, water, one or more of preservatives and one or more of colorants.

The formulation of the present invention can be prepared by any known method. In accordance to the preferred embodiment of the present invention the preferred method, for preparation the presently disclosed selfemulsifiable formulation comprises of dissolution of immunosuppression agent in hydrophilic agent followed by entrapping of solubilised immunosuppression agent with lipophilic agent, which in-turn is followed by treatment of oil entrapped solubilised form of drug with one or more of surfactants and the resulted solubilised drug entrapped with oil and one or more of surfactants is treated with preservative and antioxidant.

DETAILED DESCRIPTION AND PREFERRED EMBODIMENTS OF INVENTION

In accordance with this invention a selfemulsifiable formulation for oral administration, as described herein above, is disclosed, wherein said formulation essentially comprises of immunosuppression agent, hydrophilic agent, lipophilic agent, one or more of surfactants, antioxidant and preservative, wherein immunosuppression agent is preferably lactam macrolide having immunosuppression activity; hydrophilic agent is selected from a group consisting of pharmaceutically acceptable $C_{1-5}$ alkyl, tetrahydrofuryl diether, tetrahydrofuryl partial ether, low molecular weight monooxy-alkane-diol, low molecular weight polyoxy-alkane-diol, 1,2-propyleneglycol, ethanol; lipophilic agent is selected from a group consisting of medium chain monoglycerides, medium chain diglycerides, mixed esters of saturated fatty acids, like caprylic and/or capric acids, medium chain triglycerides of caprylic and/or capric acids; one or more of surfactant is selected from a group consisting of hydrogenated vegetable oils, polyoxyethylene sorbitan fatty acids, transesterified caprylic and/or capric glycerides; antioxidant is selected from a group consisting of alpha-tocopherol, ascorbyl palmitate, butyl hydroxy anisole, butyl hydroxy toluene, propyl gallate; preservative is selected from a group consisting of ethanol, benzyl alcohol.

In accordance to the most preferred embodiment of the present invention, it has been surprisingly found that to have particular stable microemulsions of clinically acceptable particle size with enhanced bioavailability and reduced variability in inter and intra-patient dose response, are obtained by using novel lipophilic agent of the present invention. The most preferred lipophilic agent of the present invention, which may also be referred to, as drug or immunosuppression agent carrier is medium chain triglyceride of caprylic acid and capric acid, named to as labrafac lipophile. In accordance to the preferred embodiment of the present invention the medium chain triglyceride of caprylic acid and capric acid, which is used as lipophilic agent in the presently disclosed formulation is obtained by any known method, like by esterification of glycerol by caprylic acid and capric acid at high temperature. The medium chain triglyceride of caprylic acid and capric acid, which is selected as lipophilic agent has specific gravity of about 0.93 to 0.96, refractive index of about 1.44 to 1.452, acid value less than about 0.2, saponification value of about 310 to 360 and iodine value less than about 1 and water content less than about 0.5.

In accordance to one of the preferred embodiments of the present invention immunosuppression agent is cyclosporine, particularly cyclosporine A having immunosuppression activity; hydrophilic agent is additionally selected from a group consisting of pharmaceutically acceptable lower ($C_{1-4}$) alkanols, like ethanol; alkylene glycol monoalkyl ethers, like diethylene glycol monoethyl ethers, franscutol, glycofural (known as tertrahydrofuryl) alcohol polyethylene glycol ether. The preferred hydrophilic agent is lower alkanol, preferably ethanol.

The preferred lipophilic agent is medium chain triglyceride of caprylic acid and capric acid.

The surfactant, one or more, is/are additionally selected from a group consisting of saturated polyglycolysed $C_8$ to $C_{10}$ glycerides, like transesterified caprylic and/or capric glycerides, particularly PEG-8 caprylic and/or capric acid glyceride exhibiting specific gravity of about 0.930 to 0.960, refractive index of about 1.44 to 1.452, acid value less than about 0.2, saponification value of about 85 to 105, peroxide value less than about 6.0. free glycerol content less than about 5.0%, ethylene oxide content of about 1.0 ppm, water content less than about 1.0%, capric acid less than about 2.0%, caprylic acid ($C_8$) about 50 to 80%, capric acid ($C_{10}$) about 20 to 50%, capric acid ($C_{12}$) less than about 3% and myristic acid ($C_{14}$) less than about 1.0%, hydrophilic liophilic balance, referred to as HLB, value of about 14; polyoxyethylene sorbitan fatty acid esters, like polysorbate 20, polysorbate 40, polysorbate 80, more preferably polysorbate 80; polyoxyethylene castor oil derivatives, like cremophor RH 40, cremophore EL, preferably cremophore RH 40.

The preservative, to protect the formulation during storage and use from any microbial growth, particularly in tropical region, is selected from a group consisting of ethanol, benzyl alcohol.

In accordance to the present invention the immunosuppression agent is taken in an amount of about 2 to 10%, preferably in an amount of about 5 to 10%. It is taken in ratio of about 1:05 to 1:2-5 more preferably of about 1:1.25 by weight with respect to hydrophilic agent. The hydrophilic agent is taken alone or in combination. The hydrophilic agent is taken in weight ratio of about 1:1 to 1:6. The preferably used hydrophilic agent is ethanol, which is taken in the ratio of about 1:0.5 to about 1:2.5 with respect to immunosuppression agent. The other preferred hydrophilic agent is diethylene glycol monoethyl ethers. The lipophilic agent, preferably medium chain triglyceride of caprylic and capric acids is present in the system in the ratio of immunosuppression agent to lipophilic agent of about 1:0.5 preferably of about 1:1.5 or 1:1.7 more preferably of about 1:4 by weight for entrapment of solubilised immunosuppression agent, particularly cyclosporine, more particularly cyclosporine A. The other lipophilic agents used in the present invention include capmul MCM and crodamal GTCC, which are used in the ratio of about 1:0.5 to 1:4 by weight with respect to hydrophilic agent. Still other lipophilic agent of the present invention includes combination of labrafac and labrasol are taken in the ratio of about 1:3, preferably of about 1:3.5, more preferably of about 1:4 by weight. In accordance to the present invention labrasol acts as surfactant.

The surfactants, in accordance to the present invention, include transesterified caprylic and/or capric glyceride, like labrasol, which is taken in the ratio of about 2:1, preferably of about 3:1, more preferably of about 6:1 by weight with respect to lipophilic agent of the present invention. In accordance to one of the preferred embodiments of the present invention the labrasol is used in combination with one or more of other surfactants, like cremophore RH 40 in the ratio of about 1:1, preferably of about 2.5:1 by weight or with polysorbate 80 in the ratio of about 2:1, preferably of about 4.5:1 by weight. In accordance to one of the preferred embodiment of this invention the combination of labrasol, cremophor RH 40, polysorbate 80 is taken in the ratio of about 4:1:1.5 by weight respectively which gives clear translucent microemulsions with bluish tinge and particle size less than 100 nm.

The preservative, in accordance to the present invention, includes benzyl alcohol in the amount of about 0.5 to 1% by weight.

The antioxidant, in accordance to the present invention, includes alpha-tocopherol in the amount of about 0.0007 to 0.00009.

The formulation of the present invention can be prepared by any known method. The preferred method, in accordance to one of the preferred embodiments of this invention comprises of following steps;— a) dissolution of immunosuppression agent in hydrophilic agent,
b) entrapping of solubilised immunosuppression agent with lipophilic agent,
c) treatment of oil entrapped solubilised form of drug with one or more of surfactants,
d) treatment of solubilised drug entrapped with oil and one or more of surfactants with preservative and antioxidant In accordance to the preferred method of the present invention the first step involves dissolution of selected amount of immunosuppression agent in selected amount of hydrophilic agent. The concentration of hydrophilic agent is optimized to such a level in the present invention, that it will keep the immunosuppression agent in solubilized form till the formulation shelf life. The solubilisation step of the presently disclosed method is followed by entrapping with selected amount of presently disclosed lipophilic agent, which acts as carrier during the absorption of the drug, particularly of immunosuppression agent in the gastrointestinal tract. The third step of the presently disclosed process for manufacture of presently disclosed formulation involves treatment of oil entrapped solubilised form of drug with selected amount of one or more of the surfactants. The fourth step of the presently disclosed process for manufacture of presently disclosed formulation involves treatment of solubilised drug entrapped with oil and one or more of surfactants with selected amount of the preservative and antioxidant.

In accordance to one of the preferred embodiments of the present invention the formulation is made available in a shell, preferably soft shell, wherein the said shell essentially comprises of gelatin, glycerin, water and one or more of preservatives, like methyl paraben, propyl paraben, and one or more of colorants, like iron oxide black, titanium dioxide.

In accordance to the preferred embodiment of the present invention, the formulation having presently disclosed composition and prepared in accordance to the preferred method, as described herein above is filled in the shell, preferably in the soft shell, more preferably in the disintegrating soft gelatin shell, which becomes part of the formulation for oral administration and it can not be separate entity of the medicament taken by the patient.

However, the present invention is not restricted by making availability of the formulation filled in the presently disclosed shell. It is obvious to those who have knowledge of the art that the presently disclosed formulation can also be administered in the form of solution or after filling in any of the known shell, which may be soft or hard shell. It is further obvious to those who have knowledge of the art that the presently disclosed shell can also be used for filling any other formulation including similar formulation.

Therefore, in accordance to one of the preferred embodiments the present invention a disclosure is made of shell essentially comprising of gelatin, glycerin, water and one or more of preservatives, like methyl paraben, propyl paraben, and one or more of colorants, like iron oxide black, titanium dioxide, wherein gelatin is taken in an amount of is about 35 to 50% by weight, glycerin is taken in an amount of about 15 to 30% by weight, the preservatives, like methyl paraben propyl paraben are taken in an amount of about 0.2, more preferably of about 0.8% by weight, water is taken in an amount of about 30 to 45% by weight, colorants, like iron oxide black, titanium dioxide are taken in an amount of about 0.5%.

It is obvious from the foregoing description that the advantages of the presently disclosed selfemulsifiable formulation for oral administration, as disclosed and described herein above includes increased solubility, transport rate, bioavailability and bioabsorption of the immunosuppression agent; capability of making early bioavailability of the immunosuppression agent, particularly in the upper part of the gastrointestinal tract; capability to meet satisfactorily the clinical requirements; capability to form microemulsions of particle size less than 200 nm, preferably less than 100 nm whether administered orally in the form of microemulsions mixed with fruit juice, milk or any aqueous medium, or administered orally after filling in a soft or hard shell; capability to facilitate the availability of the immunosuppression agent, preferably in the upper part of the gastrointestinal tract in less than 12 minutes, more preferably in less than 10 minutes by rupturing the shell; reduced inter and intra patient bioabsorption variability; capability to be stored in the tropical countries for a longer time; capability to form thermodynamically stable oil in water microemulsions in-situ, which are stable for more than 24 hrs and also having capability to be administered orally after filling in a soft or hard shell, or in the form of solution.

In accordance to the preferred embodiments of the present invention a novel selfemulsifiable formulation having enhanced bioabsorption, bioavailability and immunosuppression activities and comprising of a novel lipophilic system consisting of medium chain triglyceride of caprylic acid and capric acid (labrafac lipophile) and labrasol, wherein labrasol also serves as surfactant, which is combined with other selected surfactants, like cremophore RH 40 and/or polysorbate 80 is disclosed, wherein said formulation also comprises of an immunosuppression agent, hydrophilic agent antioxidant and preservative, wherein said immunosuppression agent is essentially cyclosporine having immunosuppression activity and said hydrophilic agent is preferably ethanol, said antioxidant is preferably alpha-tocopherol and said preservative is preferably benzyl alcohol, and said formulation is prepared by dissolving immunosuppression agent in hydrophilic agent followed by entrapping of solubilised immunosuppression agent with lipophilic agent and subsequent treatment with one or more of surfactants, and preservative and antioxidant, and is filled in soft-gelatine shell, which is capable of rupturing preferably in less than 10 minutes to deliver the formulation in upper part of gastrointestinal tract, wherein it forms thermodynamically stable oil in water microemulsions in-situ to have enhanced bioavailability and bioabsorption of the immunosuppression agent, which can show its enhanced immunosuppression activities thereby.

EXPERIMENTS

The presently disclosed formulations were prepared in accordance to the preferred method of preparation, as described herein above, and phase diagrams (FIG. 1), relative concentrations of various phases, i.e. oil phase, water phase and mixture of surfactants (FIG. 2), rupture identification test in dissolution medium by analysing the percent drug content at different time intervals (FIG. 3), percent amount of normalised particle size (FIG. 4) and mean plasma concentration of the drug (cyclosporine) after administration of the shell (FIG. 5) were studied/carried out in case of selected preparations XIII, XIV and/or XV.

It was observed that all formulations were observed to be clear solutions, some formulations were slightly turbid in contact with aqueous media but when subjected to particle size analysis, passes the microemulsion properties. The formulations were filled in soft gelatin shell of the present invention.

The formulations were prepared having compositions as given in FIG. 6. For experimental purpose only different combinations of said agents were used. However, the combination of experiments XIII, XIV and XV, particularly of XIV and XV were observed to better and were according to the preferred embodiments of the present invention. These experimental formulations were subjected to microemulsion tests. From these experiments it was observed that presence of labrafac lipophile as lipophile agent in combination with other selected-agents improves the microemulsion quality significantly.

Now referring to accompanying figures, the FIG. 1 shows the two way plot for cyclosporine microemulsion—phase behaviour. These phases are mixture of surfactants (I), oil phase (II) and water phase (III). Point 1 represents water in oil microemulsion existence, while point 2 represents oil in water microemulsion existence part and point 3 is coarse emulsion part while point 4 is micelle phase. According to this phase diagram, the oil phase (II) contains 10% of cyclosporine-A dissolved in hydrophilic agent and then entrapped in oil. The oil phase (II) concentration increases from 0% along the left-hand margin to 100% as shown by arrow. The concentration of aqueous phase (III) increase from 0% along the right hand margin to 100% as shown by arrow, while the concentration of surfactants mixture (I) increase from 0% at the base line of the plot to 100% as shown by arrow. The relative portion of oil, surfactants and water phases will suitably lie with the area (2), i.e. microemulsion existence field as shown in the FIG. 1. All the experiments were carried out in the laboratory at a temperature less than 25° C. having relative humidity less than 60%.

Figure 2:
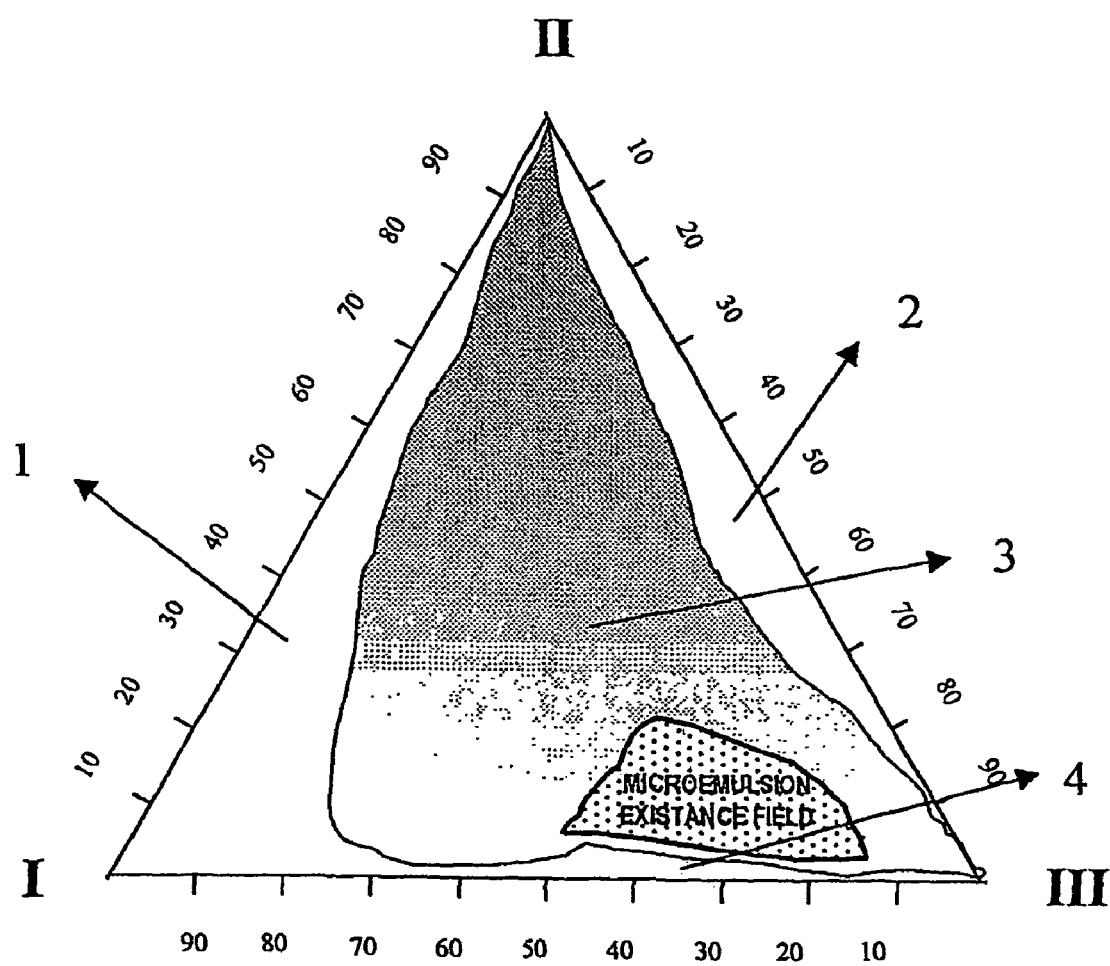
FIG. 2 shows the phase diagram representing the relative concentration of oil phase, water phase and mixture of surfactants of the selfemulsifiable formulation in accordance to the preferred embodiments of the present invention.

The FIG. 2 shows three way plot for cyclosporine microemulsion. This figure represents the relative concentration of oil phase (II), water phase (III) and mixture of surfactants (I). The point A represents the preferred concentration of microemulsion that is oil phase (II), water phase (III) and surfactant phase (I).

Figure 3:
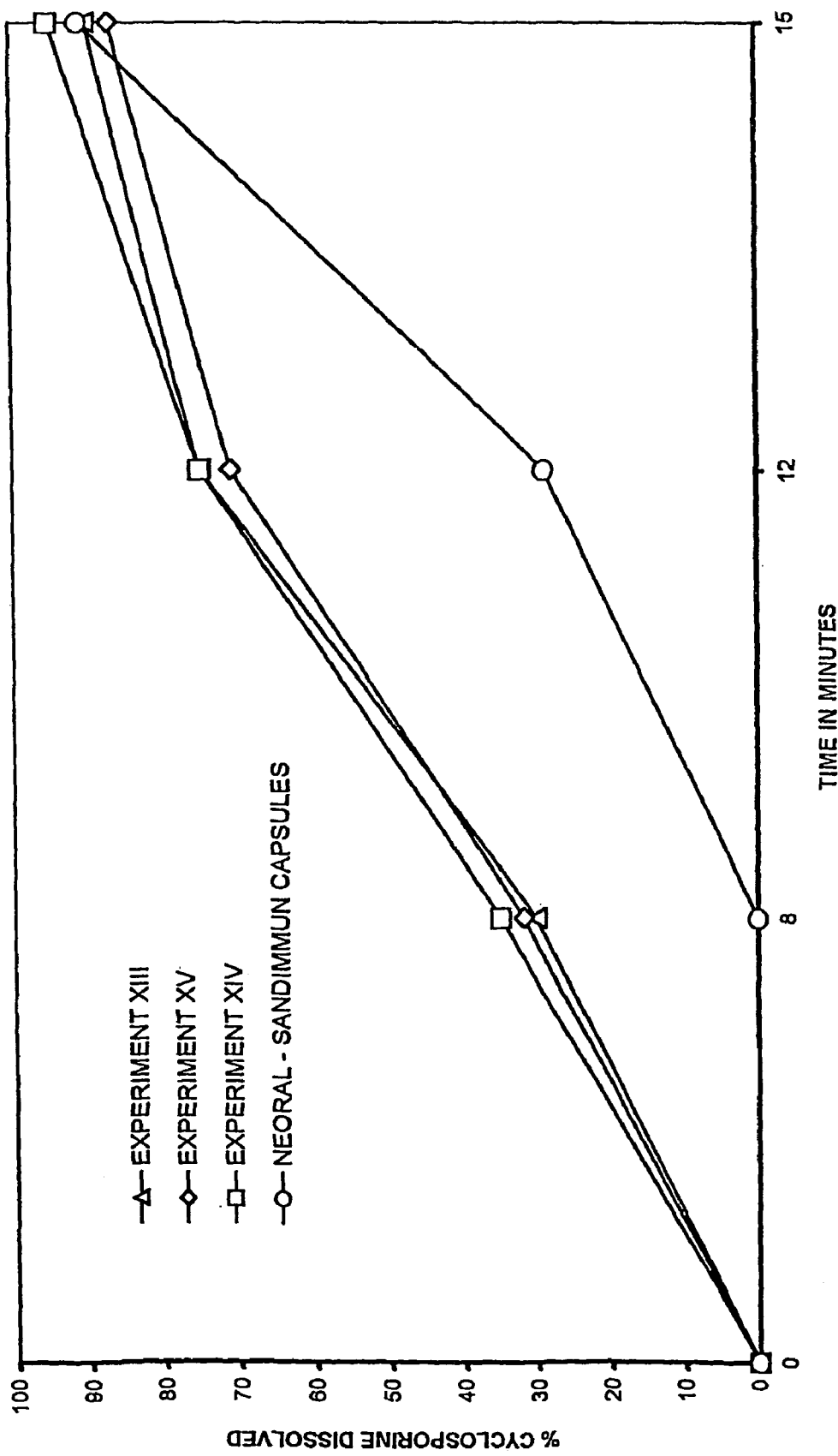
FIG. 3 shows the comparative dissolution profile of experiments XIII, XIV and XV of the selfemulsifiable formulation in accordance to the preferred embodiments of the present invention and of Sandimmun Neoral, which is taken as standard.

The FIG. 3 represents the comparative dissolution profile of experiments XIII, XIV, XV and standard experiment for which Sandimmun Neoral was taken as standard. The X-axis represents time in minutes required to rupture the shell as USP-specification for cyclosporine shells. The rupture time was identified by content analysis in the dissolution fluid. The Y-axis represents the percentage of cyclosporine dissolved in dissolution fluid, which was analysed by high performance liquid chromatography (HPLC).

In view of stringent dissolution test specification of cyclosporine capsule USP in USP/NF 24 that each capsule should rupture within 15 minutes, the presently disclosed formulation of immunosuppression agent, particularly cyclosporine was also subjected to dissolution tests as per USP specifications and tested for rupture test and shell stability test. The soft gelatin shells having following compositions were used in four set of experiments for these studies:—

| | Experiment No. | | | |
|---|---|---|---|---|
| | A | B | C | D |
| Ingredient | Composition | | | |
| Gelatin | 35% | 40% | 45% | 45% |
| Glycerine | 15% | 25% | 25% | 20% |
| Sorbitol | 18.7% | — | — | — |
| Propyl Paraben | 0.04% | 0.04% | 0.04% | 0.04% |
| Methyl Paraben | 0.76% | 0.76% | 0.76% | 0.76% |
| Colorants | 0.5% | 0.5% | 0.5% | 0.5% |
| Water | 30.0% | 33.7% | 28.7% | 33.7% |

The soft gelatin shells having above compositions were prepared in accordance to the preferred method of the present invention and were cured at lower humidity and temperature for less than 25° C. for sufficient time. The cured shells were subjected to rupture test. The in-vitro dissolution conditions were maintained as follows:—

| | |
|---|---|
| Apparatus | USP Type-II (paddle) |
| Medium | Water (500 ml) |
| Rotation per minute (RPM) | 50 |
| Temperature of medium | 37° C. |
| Time | 15 mins |

As per USP dissolution test of cyclosporine, it mentions the rupture of the shell should be within 15 mins. In the present invention, the efforts were taken not only to comply with the dissolution but also to quantify the rupture time, which gives clear identification of the rupture. The rupture identification tests have been designed and were performed in dissolution medium by analysing the percent drug content at different time intervals, viz 8, 12 and 15 minutes by HPLC). The percent drug contents for each rupture time interval are given in FIG. 3, as described herein above. The percent drug contents in case of experiments XIII, XIV, XV and standard (Sandimmun Neoral) were observed to be 30, 31.8, 35 and 0 respectively at time interval of 8 mins, and 75, 70.86, 75 and 28.73 respectively at time interval of 12 mins, and 90, 86.83, 95 and 91.01 respectively at time interval of 15 mins. This data clearly shows that the shell of the present invention releases higher amount of the drug as compared to the standard.

Figure 4:
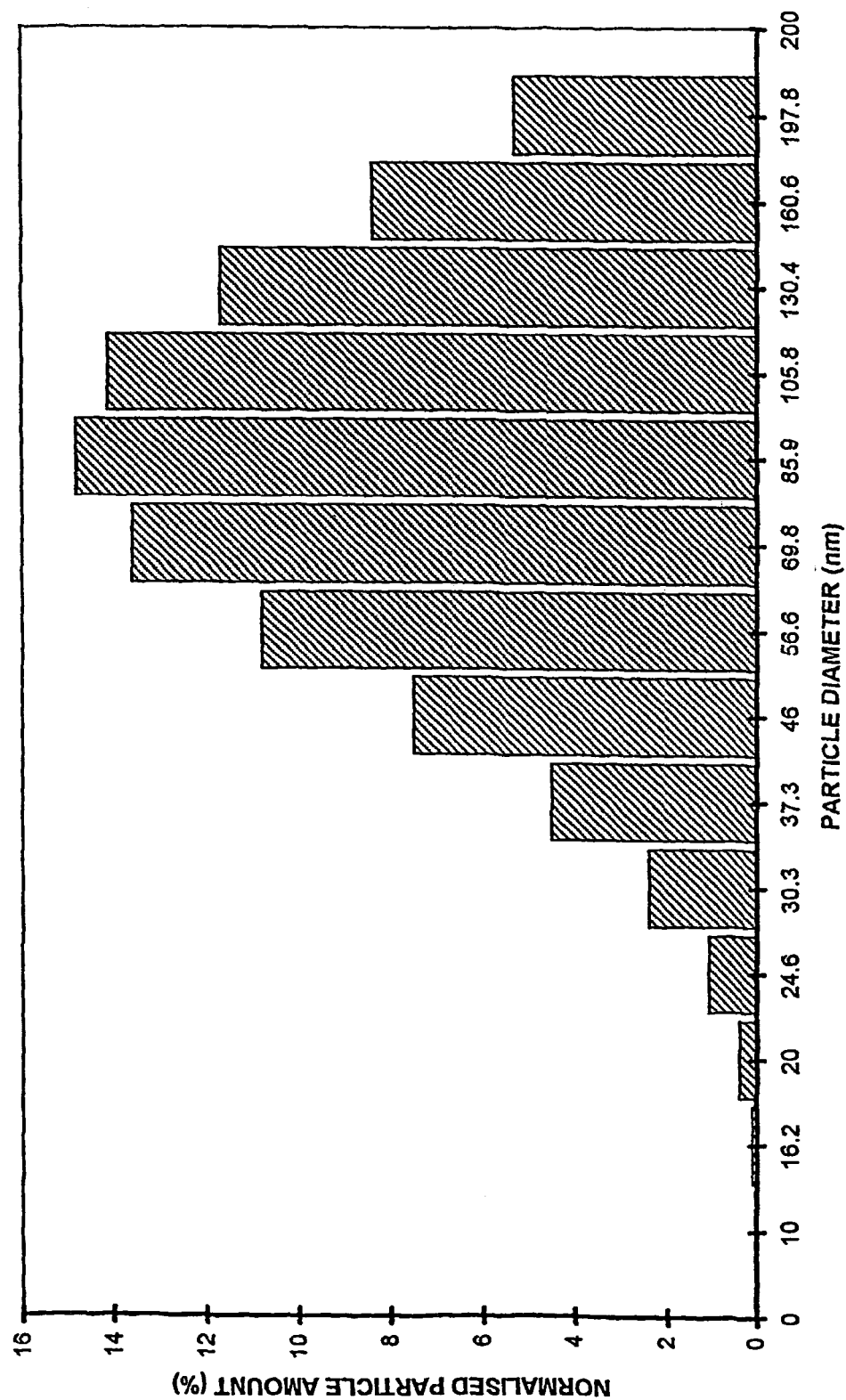
FIG. 4 shows the percent amount of normalized particle size in experiment XV, the best preferred experiment of the selfemulsifiable formulation in accordance to the preferred embodiments of the present invention.

The FIG. 4 represents percent amount of normalised particle size in experiment XV, the best mode of the present invention. The X-axis represents the particle diameter in nm and Y-axis represents the amount of normalised particle size in percent. It is observed from the figure that the mean particle size is less than 100 nm.

Figure 5:
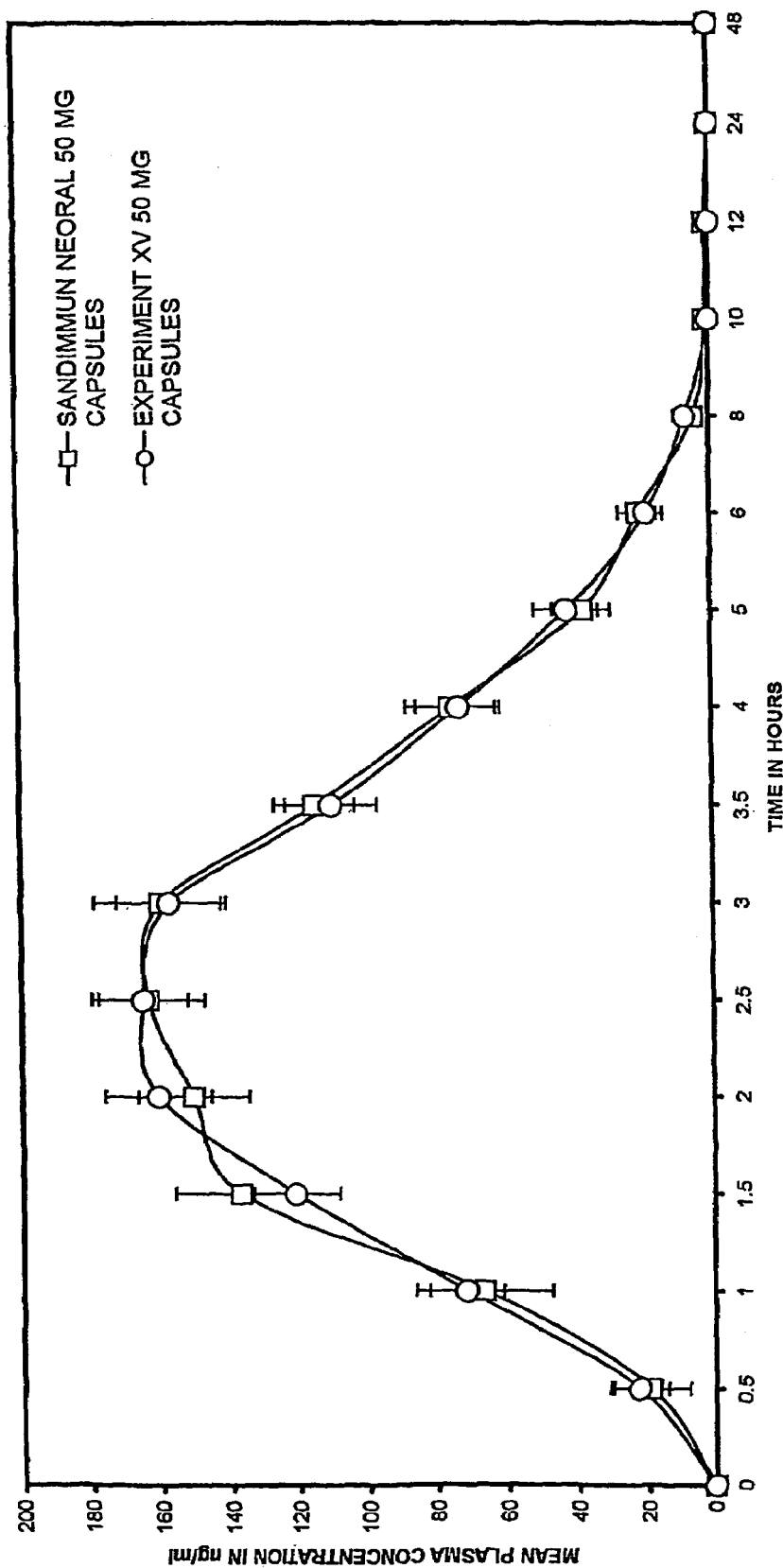
FIG. 5 shows the mean plasma concentration of the immunosuppression agent after administration of formulation, after filled in soft-shell, of experiment XV, the best preferred experiment of the selfemulsifiable formulation in accordance to the preferred embodiments of the present invention.

The FIG. 5 represents the mean plasma concentration of cyclosporine after administration of shells of the present invention of experiment XV. The X-axis represents the time in hours and Y-axis represents mean plasma concentration in ng/ml. It is observed from the figure that the mean plasma concentration that is the bioavailability of the drug is more than the standard at the early part of the gastrointestinal tract and having the less variability in the inter and intra patient for the dose response.

The presently disclosed formulation (experiment XV) was subjected to bioequivalence study and the results were compared with the standard—Sandimmun Neoral. The bioequivalence study of formulation of experiment XV, best mode of performing the present invention, was carried out on 24 healthy male subjects using 50 mg of sample of this preparation and the results were compared with 50 mg of sample of Sandimmun Neoral. All the subjects were adult, healthy, non-smoking males. The mean (±S.E.) age and weight for the subjects were 27.42±0.97 years and 63.63±1.38 kg respectively. Subjects were selected for the participation in the study after providing informed written consent and successfully completing a battery of medically related examinations including medical history, complete physical examination, electrocardiogram and a laboratory profile with hematological, urine and biochemical tests. Subjects were excluded if they had received any drug that are known to induce the drug-metabolising enzymes within three months of study entry. History of hypersensitivity to any drug was ruled out. In a randomized cross over and comparative study designed, 24 subjects received these two preparations on two occasions with a wash out period of two weeks. Subjects reported to the test facility in the evening before drug administration. No food was permitted for at least 10 hrs before the administration of the drug. Next morning after attending to the morning routine, subjects were made to lie to supine. An indwelling teflon needle was introduced in the left fore arm vein and fasting blood sample was collected. Two shells of either formulations were administered with 240 ml of water. Blood was collected in centrifuge tube containing 0.1 ml of 10% ETDA. Post dose sampling time after drug administration were 0.50, 1.00, 1.50, 2.00, 2.50, 3.00, 3.50, 4.00, 5.00, 6.00, 8.00 10.00, 12.00, 24.00 and 48.00 hrs. Blood samples were centrifuged in cooling centrifuge, maintained at −20° C.±5° C.; with appropriate labels, identifying subject numbers, study day and time of blood collection. Fluid intake was controlled and consistent for the first four hours following drug administration as follows: drug was administered with 240 ml of water, 280 ml of a non-caffeine containing soft drink provided 4.0 hrs post dose. Water was allowed ad libitum there after. Standarised breakfast, lunch and dinner were served to the subjects at 4.0, between 7 to 8 hrs and 14 hrs respectively. Emergence of symptoms, if any were noted by the subjects at the end of the study in the symptom check list formed. The subjects were housed in the laboratory for the entire period. It was randomised comparative study with a two way cross over design. Plasma cyclosporine levels were measured by HPLC method. The drug was extracted from plasma and injected on HPLC system. The chromatography was carried out on $C_{18}$ column using acetonitrile:distilled water in the ratio of 70:30 (v/v) at flow rate of 1.0 ml per min at 80° C. The detection was carried out using a UV-detector. The lowest limit of qualification of the drug from plasma 20 ng/ml.

Administration of standard formulation (Sandimmun Neoral) showed a maximum concentration of cyclosporine 218.2±16.9 ng/ml in plasma ($C_{max}$) (ln $C_{max}$ 5.2979±0.0936) at 2.42±0.16 hrs ($T_{max}$), while that of test formulation (Experiment XV) showed a maximum concentration of cyclosporine 208.5±12.8 ng/ml ($C_{max}$) (ln $C_{max}$ 5.2912±0.0673) at 2.29±0.11 hrs ($T_{max}$).

The $AUC_{(0-t)}$ for standard formulation was 518.35±50.15 ng/ml×hr (ln $AUC_{(0-t)}$ 6.1406±0.1010) and for test formulation, it was 518.71±46.97 ng/ml×hr (ln $AUC_{(0-t)}$ 6.1238±0.1163).

The $AUC_{(0-\infty)}$ for standard formulation was 611.64±54.55 ng/ml×hr (ln $AUC_{(0-t)}$ 6.3262±0.0897) and for test formulation, it was 597.27±50.13 ng/ml×hr (in $AUC_{(0-\infty)}$ 6.2847±0.1062).

The elimination rate constants for standard and test formulations were 0,140±0.023 $hr^{-1}$ and 0.168±0.028 $hr^{-1}$ and elimination half-lives were 7.98±0.97 hrs and 7.34±1.44 hrs respectively.

In this study, with both the formulations, standard and experiment XV, cyclosporine was detected in plasma in few subjects at 0.50 hrs after ingestion of formulation. Cyclosporine was detected up to 8 hrs in some of the subjects post-dose with both the formulations. $C_{max}$ values, time at which they were achieved $T_{max}$ were comparable with both the formulations, so also were $AUC_{(0-t)}$, $AUC_{(0-\infty)}$, $K_{el}$ and $T_{1/2}$. When ANOVA was applied with the subjects, period and treatment as variables no significant variation was observed for $T_{max}$, whereas subject parameter was found significant for $C_{max}$, ln $C_{max}$, $AUC_{(0-t)}$, ln $AUC_{(0-t)}$, $AUC_{(0-\infty)}$ and ln $AUC_{(0-\infty)}$.

The 90% confidence interval for cyclosporine for the $C_{max}$, $AUC_{(0-t)}$ and $AUC_{(0-\infty)}$ values were 87.26% to 104.34%, 84.10% to 117.23% and 81.76% to 114.60% respectively. For the log-transformed data they were 90.54% to 109.69%, 82.24% to 118.00% and 80.21% to 115.57% respectively. The ratio of the least squares means of the $C_{max}$ $AUC_{(0-t)}$ and $AUC_{(0-\infty)}$ of the test/standard were 95.56%, 100.07% and 97.65% respectively. For the log-transformed data the ratios were 99.87%, 99.73% and 99.34% respectively.

The power of test for cyclosporine for the $C_{max}$, $AUC_{(0-t)}$ and $AUC_{(0-\infty)}$ value was 97.44% and for log-transformed data it was 91.15%. The inter-subject variability for cyclosporine for $C_{max}$, $AUC_{(0-t)}$ and $AUC_{(0-\infty)}$ values were 17.54%, 33.18% and 33.31% respectively. For log-transformed data the values were 19.46%, 37.51% and 37.98% respectively. When $AUC_{(0-t)}$ of both the formulations were compared, experiment XV and Standimmun Neoral showed bioavailability of 100.07%.

The bioequivalence data of both the formulations—standard and experiment XV using 50 mg shells is given below. The mean (ng/ml), S.D., S.E. and COV (%) were measured at time intervals of 0.00, 0.50, 1.00, 1.50, 2.00, 2.50, 3.00, 3.50, 4.00, 5.00, 6.00, 8.00 10.00, 12.00, 24.00 and 48.00 hrs.

|  | Sandimmun Neoral | | | | Experiment XV | | | |
| --- | --- | --- | --- | --- | --- | --- | --- | --- |
| Time in hrs | Mean (ng/ml) | S.D. | S.E. | COV (%) | Mean (ng/ml) | S.D. | S.E. | COV (%) |
| 0.00 | 0.00 | 0.00 | 0.00 | 0.00 | 0.00 | 0.00 | 0.00 | 0.00 |
| 0.50 | 19.1 | 56.4 | 11.5 | 295.81 | 22.8 | 42.0 | 8.6 | 184.41 |
| 1.00 | 66.7 | 95.3 | 19.5 | 142.81 | 71.8 | 51.4 | 10.5 | 71.58 |
| 1.50 | 137.2 | 92.1 | 18.8 | 67.13 | 121.0 | 62.1 | 12.7 | 51.34 |
| 2.00 | 150.6 | 77.5 | 15.8 | 51.50 | 160.6 | 74.2 | 15.1 | 46.17 |

-continued

| | Sandimmun Neoral | | | | Experiment XV | | | |
|---|---|---|---|---|---|---|---|---|
| Time in hrs | Mean (ng/ml) | S.D. | S.E. | COV (%) | Mean (ng/ml) | S.D. | S.E. | COV (%) |
| 2.50 | 163.4 | 78.4 | 16.0 | 48.01 | 164.9 | 62.5 | 12.8 | 37.89 |
| 3.00 | 159.8 | 92.2 | 18.8 | 57.72 | 157.2 | 72.6 | 14.8 | 46.17 |
| 3.50 | 114.7 | 57.6 | 11.8 | 50.25 | 109.8 | 64.7 | 13.2 | 58.96 |
| 4.00 | 75.3 | 62.7 | 12.8 | 83.27 | 73.2 | 58.1 | 11.9 | 79.41 |
| 5.00 | 37.9 | 39.6 | 8.1 | 104.54 | 42.3 | 43.9 | 9.0 | 103.96 |
| 6.00 | 21.4 | 27.9 | 5.7 | 130.08 | 19.0 | 25.6 | 5.2 | 134.78 |
| 8.00 | 4.6 | 10.7 | 2.2 | 232.42 | 7.0 | 14.3 | 2.9 | 203.34 |
| 10.00 | 1.2 | 5.7 | 1.2 | 489.71 | 0.0 | 0.0 | 0.0 | 0.0 |
| 12.00 | 1.1 | 5.5 | 1.1 | 490.04 | 0.0 | 0.0 | 0.0 | 0.0 |
| 24 | 0.0 | 0.0 | 0.0 | 0.0 | 0.0 | 0.0 | 0.0 | 0.0 |
| 48 | 0.0 | 0.0 | 0.0 | 0.0 | 0.0 | 0.0 | 0.0 | 0.0 |
| $AUC_{(0-t)}$ | 518.35 | 245.75 | 50.16 | 47.41 | 518.72 | 230.14 | 46.98 | 44.37 |
| $AUC_{(0-t)}$ | 611.64 | 267.32 | 54.57 | 43.70 | 597.27 | 245.61 | 50.14 | 41.12 |

The mean and ±SEM of both the preparations for $C_{max}$ (ng/ml), ln $C_{max}$, $T_{max}$, $AUC_{(0-t)}$ (ng/ml*hr), ln $AUC_{(0-t)}$, $AUC_{(0-\infty)}$ (ng/ml*hr), ln $AUC_{(0-\infty)}$, $T_{1/2}$ hr and $K_{el}$/hr are given below:

| | Preparation | | | |
|---|---|---|---|---|
| | Sandimmun Neoral | | Experiment XV | |
| Parameter | Mean | ± SEM | Mean | ± SEM |
| $C_{max}$ | 218.2 | 16.9 | 208.5 | 12.8 |
| ln $C_{max}$ | 5.2979 | 0.0936 | 5.2912 | 0.0673 |
| $T_{max}$ | 2.42 | 0.16 | 2.29 | 0.11 |
| $AUC_{(0-t)}$ | 518.35 | 50.15 | 518.71 | 46.97 |
| ln $AUC_{(0-t)}$ | 6.1406 | 0.1010 | 6.1238 | 0.1163 |
| $AUC_{(0-\infty)}$ | 611.64 | 54.55 | 597.27 | 50.13 |
| ln $AUC_{(0-\infty)}$ | 6.3262 | 0.0897 | 6.2847 | 0.1062 |
| $T_{1/2}$ | 7.98 | 0.97 | 7.34 | 1.44 |
| $K_{el}$ | 0.140 | 0.023 | 0.168 | 0.028 |

The above bioequivalence data shows that the trial of composition of formulation of experiment XV has less percentage of Coefficient of Variation (COV) and standard error (SE) than the standard formulation. From this data, it can be concluded that the presently disclosed formulation shows significantly less variability in inter and intra patient dose response than the standard formulation, which is a unique characteristic required for the formulation, particularly for the cyclosporine formulation microemulsions. From the above bioequivalence data, one another advantage of the presently disclosed formulation which is apparent, is that the soft gelatin shell having very low rupture time, that is, about 8 mins, will give fast release of the drug out of the formulation for the immediate bioavailability of the drug, that is, of the immunosuppression agent, that is, of the cyclosporine, i.e. 22.8 ng/ml in 30 mins as against standard formulation i.e. 19.1 ng/ml.

The invention claimed is:

1. A selfemulsifiable formulation for oral administration, wherein said formulation is consisting essentially of immunosuppression agent, hydrophilic agent, lipophilic agent, surfactants, antioxidant and preservative, wherein said immunosuppression agent is cyclosporine-A having immunosuppression activity and is taken in an amount of about 2 to 10% by weight of the formulation;

said hydrophilic agent is consisting essentially of ethanol taken in a weight ratio of about 1:0.5 to 1:2.5 with respect to said immunosuppression agent;

said lipophilic agent is medium chain triglycerides of caprylic and capric acids taken in a ratio of immunosuppression agent to lipophilic agent of about 1:1.5 or about 1:1.7 by weight;

said surfactants are combination of polyglycolised transesterified caprylic and capric glycerides having a hydrophilic lipophilic balance (HLB) of about 14 and a saponification value of about 85 to 105, polysorbate 80 and cremophor RH 40;

said antioxidant is selected from the group consisting of alpha-tocopherol ascorbyl palmitate, butyl hydroxy anisole, butyl hydroxy toluene, and propyl gallate; and said preservative is selected from one of ethanol and benzyl alcohol wherein said formulation forms microemulsions of particle size less than 200 nm on contact with gastric juice or aqueous medium.

2. A selfemulsifiable formulation, as claimed in claim 1, wherein said medium chain triglyceride of caprylic acid and capric acid has specific gravity of about 0.93 to 0.96, refractive index of about 1.44 to 1.46, acid value less than about 0.2, saponification value of about 310 to 360, iodine value less than about 1 and water content less than about 0.5.

3. A selfemulsifiable formulation, as claimed in claim 1, wherein said immunosuppression agent is taken in an amount of about 5 to 10%.

4. A selfemulsifiable formulation, as claimed in claim 1, wherein said immunosuppression agent and hydrophilic agent are taken in ratio of about 1:0.5 to 1:2.5, or of about 1:1.25 by weight.

5. A selfemulsifiable formulation, as claimed in claim 1, wherein said polyglycolised transesterified caprylic and capric glycerides (Labrasol®) is taken in the ratio of about 2:1, or of about 3:1, or of about 6:1 by weight with respect to lipophilic agent.

6. A selfemulsifiable formulation, as claimed in claim 1, wherein said polyglycolised transesterified caprylic and capric glycerides (Labrasol®) and cremophor RH 40 are taken in the ratio of about 1:1, or of about 2.5:1 by weight, and said "polyglycolised transesterified caprylic and capric glycerides (Labrasol®) and polysorbate 80 are taken in the ratio of about 2:1, or of about 4.5:1 by weight."

7. A selfemulsifiable formulation, as claimed in claim 1, wherein said polyglycolised transesterified caprylic and capric glycerides (Labrasol®), polysorbate 80 and cremophor RH 40 are taken in the ratio of about 4:1:1.5 by weight respectively.

8. A selfemulsifiable formulation, as claimed in claim 1, wherein said preservative is benzyl alcohol and is taken in the amount of about 0.5 to 1% by weight.

9. A selfemulsifiable formulation, as claimed in claim 1, wherein said antioxidant is alpha-tocopherol and is taken in the amount of about 0.00007 to 0.00009%.

10. A selfemulsifiable formulation, as claimed in claim 1, wherein said formulation forms microemulsions of particle size less than 100 nm on contact with gastric juice or aqueous medium.

11. A method of preparation of selfemulsifiable formulation, said formulation consisting essentially of immunosuppression agent, hydrophilic agent, lipophilic agent, surfactants, antioxidant and preservative, wherein said immunosuppression agent is cyclosporine-A having immunosuppression activity and is taken in an amount of about 2 to 10% by weight of the formulation;

said hydrophilic agent is consisting essentially of ethanol taken in a weight ratio of about 1:0.5 to 1:2.5 with respect to said immunosuppression agent;

said lipophilic agent is medium chain triglycerides of caprylic and capric acids taken in a ratio of immunosuppression agent to lipophilic agent of about 1:1.5 or about 1:1.7 by weight;

polysorbate 80, and cremophor RH 40" has been amended to "said surfactants are combination of polyglycolised transesterified caprylic and capric glycerides having a hydrophilic lipophilic balance (HLB) of about 14 and a saponification value of about 85 to 105, polysorbate 80 and cremophor RH 40"

said antioxidant is selected from the group consisting of alpha-tocopherol ascorbyl palmitate, butyl hydroxy anisole, butyl hydroxy toluene, and propyl gallate; and said preservative is selected from one of ethanol and benzyl alcohol wherein said formulation forms microemulsions of particle size less than 200 nm on contact with gastric juice or aqueous medium and wherein said method comprising the following steps;— a) dissolution of immunosuppression agent in hydrophilic agent, b) entrapping of solubilised immunosuppression agent with lipophilic agent, c) treatment of oil entrapped solubilised form of drug with combination of surfactants, d) treatment of solubilised drug entrapped with oil and combination of surfactants with preservative and antioxidant.

12. A selfemulsifiable formulation, as claimed in claim 1, wherein said formulation is made available in a soft shell, wherein said shell is consisting essentially of gelatin, glycerin, water and one or more of preservatives, selected from the group consisting of methyl paraben, and/or propyl paraben, and one or more of colorants, such as iron oxide black or titanium dioxide.

13. A selfemulsifiable formulation, as claimed in claim 12, wherein said gelatin is taken in an amount of about 35 to 50% by weight.

14. A selfemulsifiable formulation, as claimed in claim 12, wherein said glycerin is taken in an amount of about 15 to 30% by weight of the shell.

15. A selfemulsifiable formulation, as claimed in claim 12, wherein the preservatives are taken in an amount of about 0.2%, or of about 0.8% by weight of the shell.

16. A selfemulsifiable formulation, as claimed in claim 12, wherein water is taken in an amount of about 30 to 45% by weight of the shell.

17. A selfemulsifiable formulation, as claimed in claim 12, wherein said colorant is taken in an amount of about 0.5% by weight of the shell.

18. A selfemulsifiable formulation, as claimed in claim 1, wherein said formulation is administered for immunosuppression therapy.

* * * * *